United States Patent [19]

Fukuoka et al.

[11] Patent Number: 5,475,233

[45] Date of Patent: Dec. 12, 1995

[54] METHOD AND APPARATUS FOR DETERMINING THE FIBER ORIENTATION OF PAPER BY MEASURING THE INTENSITY OF A LIGHT BEAM AT EIGHT OR MORE LOCATIONS DISTRIBUTED ON THE CIRCUMFERENCE OF A CIRCLE

[75] Inventors: Kazuhiko Fukuoka, Tokyo; Takeji Inadome, Tokorozawa; Yuji Abe, Tokyo; Akio Hatano, Kawasaki, all of Japan

[73] Assignee: Nippon Paper Industries Co., Ltd., Japan

[21] Appl. No.: 202,530

[22] Filed: Feb. 25, 1994

[30] Foreign Application Priority Data

Feb. 26, 1993 [JP] Japan .................................. 5-062581

[51] Int. Cl.⁶ .................................................. G01N 21/86
[52] U.S. Cl. .......................... 250/559.1; 356/429; 250/225
[58] Field of Search ................................. 250/225, 559, 250/562, 571, 572; 356/237, 429, 430

[56] References Cited

U.S. PATENT DOCUMENTS 4,092,068  5/1978  Lucas et al. ............................ 250/572
4,180,830  12/1979  Roach ..................................... 356/237
5,252,836  10/1993  Matthews et al. ...................... 356/445

Primary Examiner—Stephone B. Allen
Attorney, Agent, or Firm—Heneveld, Cooper, DeWitt & Litton Price

[57] ABSTRACT

A method and apparatus for rapidly and accurately determining fiber orientation of paper which is at a standstill or moving in a paper machine employs a projector which projects a light beam perpendicularly to an incident surface of the paper to be tested. The light beam reflected by the incident paper surface is caught by eight or more light receivers distributed on a circumference of a circle on the incident surface side of the paper. The circle is defined in a plane extending in parallel to the paper surface and having an axis at the point where the above-mentioned parallel plane intersects an axis of the incident light beam. A light information signal output from the light receivers are subjected to a processing to obtain the fiber orientation characteristics, such as fiber orientation index value and fiber orientation angle.

15 Claims, 9 Drawing Sheets

METHOD AND APPARATUS FOR DETERMINING THE FIBER ORIENTATION OF PAPER BY MEASURING THE INTENSITY OF A LIGHT BEAM AT EIGHT OR MORE LOCATIONS DISTRIBUTED ON THE CIRCUMFERENCE OF A CIRCLE

BACKGROUND OF THE INVENTION

1. Field of the Invention

The present invention relates to method and apparatus for determining fiber orientation, and more particularly to such a method and apparatus which is suitable for determining the fiber orientation characteristics of paper in a process of paper making.

2. Prior Art

To make paper of high quality, it is essential to determine paper quality as well as fiber orientation characteristics of the paper obtained as finished product. Devices for such determination are already well known from, for example Japanese patent application Disclosure Gazette No. Hei 4-57983 (1992-57983), disclosing a non-contact orientation meter, and Japanese patent application Disclosure Gazette No. Hei 4-113205 (1992-113205), disclosing a fiber orientation determining apparatus, both of which utilize incidence and reflection of a light beam on a surface of paper to be tested.

The apparatus disclosed in the above-mentioned Disclosure Gazette No. 1992-57983 generally comprises a projector. This apparatus also comprises a rotatable diaphragm mechanism having a slit through which the light beam projected from the projector is guided and thereby converted to a narrow linear light beam (i.e., band-like light beam) with a variable longitudinal direction. A single light receiver is adapted to catch the band-like light beam which has been incident upon the paper surface at a predetermined angle and then reflected by the paper surface. In view of the fact that the maximum reflection factor is reached when the longitudinal direction of the bandlike light beam comes in coincidence with the fiber orientation (i.e., fiber orientation angle), the differential reflection factor with respect to the band-like light beam having the variable longitudinal direction is determined to calculate the fiber orientation index value characterizing the measure of the fiber orientation.

The apparatus disclosed in the above-mentioned Disclosure Gazette No. 1992-113205 generally comprises a projector and a rotatable sample carriage on which the paper to be tested is set and illuminated with the light beam projected from the projector. A single light receiving means is adapted to catch the light beam reflected by the paper surface. The fiber orientation index value and the fiber orientation angle are calculated from the intensity of the reflected light beam and a rotating angle of the sample carriage.

The primary purpose of paper fiber orientation characteristics is to determine the quality of the paper, which information is used to control the quality of the paper. It is therefore desired that such determination can be carried out in an online mode during the process of paper making. For example, in a paper machine comprising a wire part, a press part and a dryer part, it is important that the result of such determination should be effectively reflected in a material supply to the wire part, as well as a change in the operation of the wire part. This is important because the definite orientation characteristics of the paper are substantially given when the material dispersed in water is supplied to the wire part and during conveyance of the material along the wire part.

However, none of the above-mentioned fiber orientation determining apparatuses of prior art is suitable for such on-line determination since they include the rotatable members which employ time consuming processing. Additionally, with the apparatus disclosed in the above-mentioned Disclosure Gazette No. 1992-1113205, involving rotation of the sample carriage, it is impossible to rotate the paper web in a process of paper making. In this apparatus, the optical system comprising the projector means and the light receiving means might be rotated instead of the sample carriage to obtain an equivalent optical effect. However, the paper web will continue to move during rotation of the optical system and consequently the point to be measured also moves, so it is difficult to measure the same point, and thereby to accurately determine the fiber orientation of the paper web moving in the paper machine. Also, with the apparatus disclosed in the above-mentioned Disclosure Gazette No. 1992-57983, the band-like light beam is rotated, making it difficult to accurately determine the fiber orientation of the paper web moving in the paper machine.

SUMMARY OF THE INVENTION

Accordingly, it is a principal object of the invention to provide a method and apparatus for determining the fiber orientation of paper allowing the orientation characteristics to be determined on-line so as to feed back a result of the determination to a paper machine and thereby to make high quality paper.

The object set forth above is achieved, according to one aspect of the invention, by a method for determining the fiber orientation of paper including a step of projecting an unpolarized light beam perpendicularly to a surface of paper which is at a standstill or moving. A light beam reflected by the surface of the paper is detected in substantially the same instant at eight or more locations distributed on a circumference of a circle defined in a plane extending in parallel to the paper surface on the incident side of the unpolarized light beam around a point at which an axis of an incident light beam intersects the plane. Fiber orientation characteristics of the paper are calculated, such as fiber orientation index value and a fiber orientation angle, from the intensity of the reflected light beam. When it is desired to perform said determination for paper moving in the paper machine, the object is achieved, according to another aspect of the invention, by a method for on-line determination of the fiber orientation of paper, including a step of projecting an unpolarized light beam perpendicularly to a surface of the paper moving in a paper machine. A light beam reflected by the surface of the paper is detected at substantially the same instant at eight or more locations which are distributed on a circumference of a circle defined in a plane extending in parallel to the paper surface on the incident side of said unpolarized light beam around a point at which an axis of an incident light beam intersects said plane. A spot on the surface of the paper being illuminated is scanned by said unpolarized light beam transversely of said paper machine. A fiber orientation characteristic of the paper, such as the fiber orientation index value and fiber orientation angle, are calculated from an intensity of said reflected light beam.

To determine the differential fiber orientation characteristics on both surfaces of paper at a standstill or moving in a paper machine, unpolarized light beams are projected perpendicularly to both surfaces of the paper facing the felt and the wire, respectively. The light beams reflected by the respective sides of the paper are detected by respective receivers. Preferably, the intensity of the reflected light beam which is measured is the intensity of the polarized light beam oscillating perpendicularly to the plane including an axis of the incident light beam and an axis of the reflected light beam, or the polarized light beam oscillating in parallel to the plane including an axis of the incident light beam and an axis of the reflected light beam separated from the light beam reflected by the paper surface. To further improve the accuracy of the determination, the light beam reflected by the paper surface is detected at locations distributed at substantial equal angular intervals on the circumference of circle defined around the point at which the axis of the incident light beam intersects said plane extending in parallel to the paper surface on the incident side of the unpolarized light beam.

The object set forth above is achieved, according to another aspect of the invention, by an apparatus for determining the fiber orientation of paper. The apparatus includes a projector to project an unpolarized light beam perpendicularly to a surface of paper which is at a standstill or moving. Eight or more light receivers are distributed on a circumference of a circle defined in a plane extending parallel to the surface of the paper on side of the paper upon which the unpolarized light beam is incident. The circle is around a point at which an axis of the incident light beam intersects the plane to catch a light beam reflected by the surface of the paper. A light information processor is adapted for suitably processing a signal representing an intensity of the reflected light beam measured by each of the light receivers and applied to said processor to output a light intensity information signal. An arithmetic circuit calculates fiber orientation characteristics, such as a fiber orientation index value and a fiber orientation angle, from the output signal of the light information processor.

To facilitate installation on a paper machine, the invention provides an apparatus for determining the fiber orientation of paper. The apparatus includes a projector to project an unpolarized light beam perpendicularly to a surface of the paper moving in the paper machine. Eight or more light receivers are distributed on the circumference of a circle. The circle defined in a plane extending in parallel to the surface of the side of the paper upon which the unpolarized light beam is incident, and has a center point at where the axis of an incident light beam intersects this plane. The receivers include respective photoconductive elements adapted to catch a light beam reflected by said surface of the paper, and a light information processor adapted for suitably processing a signal representing an intensity of the reflected light beam measured by each of said light receivers. The intensity signal is applied to the processor to output a light intensity information signal, an arithmetic circuit to calculate fiber orientation index value and a fiber orientation angle from the output signal of said light information processor, and the projector and the light receiver scan the paper transversely of the paper machine.

In order to determine the differential fiber orientation characteristics on both surfaces of paper which is at a standstill, or moving in the paper machine, projectors are provided which are adapted to illuminate respective surfaces of the paper which face the felt and the wire, respectively. The light receivers are adapted to catch the light beams reflected by the respective surfaces of the paper. Each of the light receivers includes no polarizer, a polarizer adapted to separate the polarized light beam oscillating perpendicularly to the plane including an axis of the incident light beam and an axis of the reflected light beam, or a polarizer adapted to separate the polarized light beam oscillating in parallel to the plane including the axis of the incident light beam and the axis of the reflected light beam. To further improve the accuracy of the determination, the eight or more light receivers are distributed at substantially equal angular intervals around the circumference of the circle defined around the point at which the axis of the incident light beam intersects the plane extending in parallel to the paper surface.

According to the invention, the projector projects the unpolarized light beam perpendicularly to the paper surface and the light beam reflected by the paper surface is caught by a plurality of light receivers distributed on the circumference of the circle. The circle is defined on the incident side of the unpolarized light beam, in the plane extending in parallel to the paper surface around the point at which the plane parallel to the paper surface intersects the axis of the incident light beam so that the angle included between the axes of incident and reflected light beams is the same for every one of the light receivers. Accordingly, unevenness in the intensity of the reflected light beam caught by the respective light receivers reflects the orientation characteristics of the paper surface. The fiber orientation characteristics, such as the fiber orientation index value and the fiber orientation angle, can be obtained from the unevenness in the intensity of the reflected light beam.

The apparatus according to the invention allows the reflected light beam to be caught by a plurality of light receivers at the same time so that the same spot on the paper surface can be rapidly measured, since the optical system for measurement includes no rotatable member. In this manner, the apparatus can be easily installed on a paper machine to determine the fiber orientation characteristics of a paper web moving at a high speed.

BRIEF DESCRIPTION OF THE DRAWINGS

The method and apparatus for determining the fiber orientation of paper according to the invention will be described with respect to a specific embodiment shown by the accompanying drawings, in which.

DETAILED DESCRIPTION OF THE PREFERRED EMBODIMENTS

Figure 1:
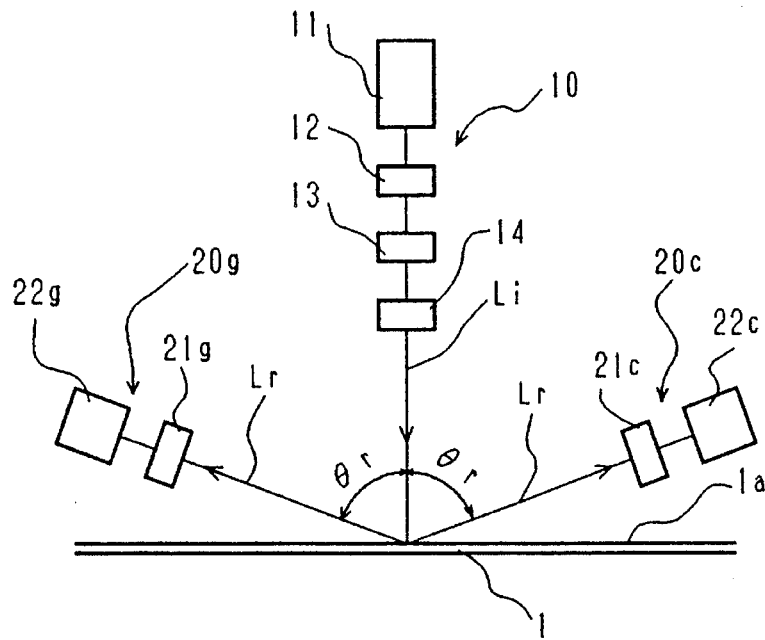
FIG. 1 is a side view schematically showing an arrangement of a measuring system as a component of the apparatus constructed according to the invention.

Referring initially to FIG. 1, a side schematic view of a fiber orientation determining apparatus is shown. The apparatus includes a projector 10 above a surface 1a of paper 1 to be tested with respect to its fiber orientation characteristics. Projector 10 includes a semiconductor laser 11, a lens 12, a polarizer 13 and a quarter undulation plate 14, arranged such that a laser beam emitted from the semiconductor laser 11 passes through the lens 12, the polarizer 13 and the quarter undulation plate 14 to form a circular polarized light beam Li. The circular polarized light beam is a light beam propagating with a direction of polarization which rotates and should be distinguished from an unpolarized light beam having no polarization characteristics. However, it can be practically considered to be an unpolarized light beam since the direction of polarization is rotated in a rotation cycle which is usually short, being on the order of $10^{-15}$ sec. Obviously, it is also possible to employ a projector comprising a halogen lamp, or the like, emitting an unpolarized light beam, and a lens system serving as a collimator for this unpolarized light beam. Projector 10 is positioned so as to project the circular polarized light beam Li perpendicularly to the paper surface 1a.

Figure 2:
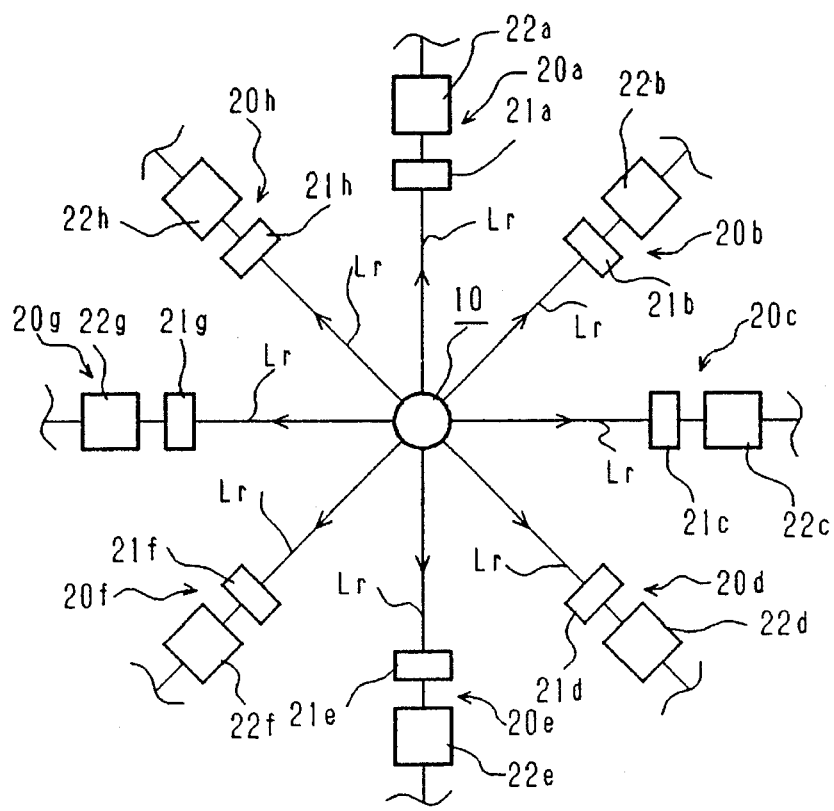
FIG. 2 is a top plan view schematically showing the arrangement of the measuring system as the component of the apparatus constructed according to the invention.

Eight light receivers, 20a–20h, respectively, comprise, as shown in FIG. 2, polarizes 21a–21h and photoconductive elements 22a–22h adapted to convert light intensities to corresponding electric signals. As shown in FIG. 1, these light receivers 20a–20h are arranged at regular intervals on the circumference of circle defined in a plane extending in parallel to the paper surface 1a around an intersecting point of said plane and an axis of said circular polarized light beam Li incident thereupon. These light receivers 20a–20h have their light receiving surfaces arranged so as to face the point at which the axis of the incident circular polarized light beam Li and the paper surface 1a intersect each other. Thus, the laser beam emitted from projector 10 is reflected on the paper surface 1a and this reflected light beam Lr is caught by the respective light receivers 20a–20h.

Specifically, the reflected light beam Lr caught by the light receivers 20a–20h is incident on the photoconductive elements 22a–22h after being separated as a predetermined polarized light beam by passage through the respective polarizers 21a–21h. The angle Θr included between the incident light beam and the reflected light beam falls within a range of 0 degrees <Θr<90 degrees, and it is preferred to select a relatively large angle Θr and thereby to obtain a correspondingly high reflection factor of the light beam reflecting the fiber orientation.

If the light receivers 20a–20h are locally crowded on the circumference of the circle, it would be impossible to obtain accurate characteristics of the fiber orientation because only directionally one-sided data could be sampled from the paper surface 1a. Accordingly, it is important to arrange the light receivers 20a–20h on the circumference of circle at substantially regular intervals. It should be understood, however, that the light receivers 20a–20h may be arranged so as to achieve optimal capture of the reflected light beam Lr when arranged at regular intervals which occur, for example, when the fiber orientation of a paper web on a paper machine can be presumed to be substantially in coincidence with a producing direction of the paper machine.

Each of the polarizers 21a–21h constituting the light receivers 20a–20h, respectively, is adapted to separate the polarized light beam oscillating in parallel to the plane including an axis of the incident light beam Li and an axis of the reflected light beam Lr or to separate the polarized light beam oscillating perpendicularly to the plane including an axis of the incident light beam Li and an axis of the reflected light beam Lr. Namely, depending on the type of polarizer 21a–21h employed, the photoconductive elements 22a–22h will catch only the polarized light beam oscillating in parallel to the plane including an axis of the incident light beam Li and an axis of the reflected light beam Lr, or only the polarized light beam oscillating perpendicularly to the plane including an axis of the incident light beam Li and an axis of the reflected light beam Lr. Alternatively, the reflected light beam Lr may be directly caught by the photoconductive elements 22a–22h without use of said polarizers 21a–21h and, therefore, without separation of the polarized light beam. In any case, the reflection factor of the light beam representing the fiber orientation reaches the maximum level when the polarized light beam oscillates perpendicularly to the plane including an axis of the incident light beam Li and an axis of the reflected light beam Lr. It is therefore preferred to measure intensities of the reflective light beam Lr using the polarizers 21a–21h each adapted to separate such polarized light beam.

Figure 3:
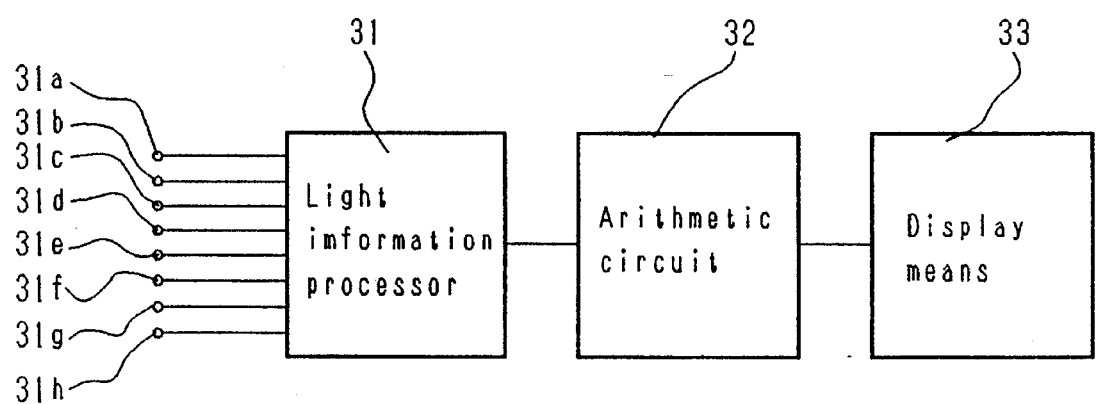
FIG. 3 is a circuit block diagram schematically showing a manner in which the light information signal is arithmetically processed in the apparatus of the invention.

As will be apparent from FIG. 3, respective output terminals of the photoconductive elements 22a–22h are respectively connected to corresponding input terminals 31a–31h of a light information processor 31 so that the intensities of the reflected light beam Lr caught by the photoconductive elements 22a–22h are converted to corresponding electric signals and then input to said light information processor 31. The light intensity information signals thus input are suitably signal-processed to provide a light information signal containing the intensity F of the reflected light beam Lr caught by the respective photoconductive elements 22a–22h and posture angle Θ of the photoconductive elements 22a–22h on the circumference of the circle defined around the axis of the incident light beam Li. There is provided on the output side of the light information processor 31 an arithmetic circuit 32. The arithmetic circuit 32 calculates, from the light information signal input thereto, an orientation index value representing a measure of the fiber orientation on the paper surface 1a and an orientation angle α representing a direction of the fiber orientation on the paper surface 1a, according to an equation as follows:

$$F(\Theta)=C(1+\eta \cos 2(\Theta-\alpha)) \tag{1}$$

where F represents the light intensity and Θ represents the posture angle of the respective light receiving means 20a–20h, as have already been mentioned, and C represents a mean intensity value of the reflected light beam. Equation (1) is a part of the Fourier series which is known as a periodic function conventionally used to approximate the fiber orientation of the paper from the data acquired. Alternatively, it is also possible to use the function other than said equation (1) such as Von Mises function or elliptic function.

Data such as the orientation index value η and the orientation angle α calculated by arithmetic circuit 32 are displayed on display 33. The display device may include a CRT connected to the arithmetic circuit 32 or a printer, or plotter, connected to said arithmetic circuit 32.

When the orientation characteristics of a paper sheet sample cut in a small-sized format are determined using the paper fiber orientation determining apparatus described above, a sample carriage on which the sample is attached may be moved in a predetermined direction relative to the apparatus which is fixed in place. Alternatively, the apparatus may be moved relative to the sample carriage which is fixed in place. In either case, desired data is acquired from which a two-dimensional distribution of the fiber orientation can be derived. If the determination is performed on two sides of the sample, the fiber orientation distribution can be measured on both the surface of the paper sample facing the wire and the surface of the paper sample facing the felt. This allows a differential fiber orientation distribution to be derived from the results of the measurements carried out on two sides of the sample.

When it is desired to determine the fiber orientation characteristics of the paper web moving in the paper machine, there are provided on transversely opposite sides of the paper machine supporting posts between which a guide rail extends so that the fiber orientation determining apparatus may be movably guided on the paper machine along the guide rail. The fiber orientation determining apparatus may be guided along the guide rail in the cross-machine direction so as to scan the paper web in order to determine the fiber orientation characteristics of the paper web both in the cross-machine direction and in the machine direction. The apparatus may be provided on the side of the paper web adjacent the wire and on the side of the paper web adjacent the felt so as to scan the paper web in the cross-machine direction and determine a differential fiber orientation characteristic of two surfaces of the paper web, both in the machine direction and in the cross-machine direction. Without operation of scanning, the fiber orientation characteristics of the paper web can only be obtained in the machine direction.

A reduction to practice of the fiber orientation determining apparatus for paper was used to acquire data on the fiber orientation of the sample paper sheet and, from the respective tests, results as will be described, were obtained.

Test 1

A semiconductor laser 11 with a wavelength of 670 nm and the maximum output of 20 mW was incorporated in the projector means 10 and silicon photodiodes were used as the photoconductive elements 22 and the fiber orientation characteristics of PPC paper having a weight per unit area of 64 g/m² were determined. The determination was repeated with the number of the light receivers 20 having been varied in number for each determination, such that from two to twenty light receivers 20 were used. The light receivers 20 were arranged substantially at equal angular distances on a circumference of a circle which is parallel to the paper surface. In addition, the determination was carried out with the light receivers 20 each having no polarizer 21, with the light receivers 20 each having a polarizer 21 adapted to separate the polarized light beam oscillating perpendicularly to the plane including an axis of the incident light beam Li and an axis of the reflected light beam Lr, and with the light receiver 20 each having the polarizer 21 adapted to separate the polarized light beam oscillating in parallel to the plane including an axis of the incident light beam Li and an axis of the reflected light beam Lr, and the results of the respective determinations are set forth below in Table 1.

drum operating at various rotations per minute (rpm) as well as various speeds of pulp slurry fed in the form of a jet stream so as to obtain various fiber orientations. For each sample, orientation of the dyed fibers relative to the rotational direction of the sheet drum, as well as the number of the dyed fibers presenting the orientation, were determined. Then, the fiber orientation determining apparatus similar to that employed in Test 1, but provided with eight light receivers 20 was used to test each sample as the angle Θr included between incident and reflected light beams was adjusted to 30 degrees, 50 degrees and 70 degrees, respectively. Thereafter, the determination was performed for three cases in which each light receivers 20 includes no polarizer 21, each light receivers 20 includes a polarizer 21 adapted to separate the polarized light beam oscillating perpendicularly to the plane including an axis of the incident light beam Li and an axis of the reflected light beam Lr and each light receiving means 20 includes a polarizer 21 adapted to separate the polarized light beam oscillating in parallel to time plane including an axis of the incident light beam Li and an axis of the reflected light beam Lr. The orientation index values, as well as the orientation angles calculated from the actual determination by the conventional method and from the determination by the apparatus of the invention, were comparatively shown by FIGS. 4–12, of which

TABLE 1

| Number of light receiving means | Using no polarizer | | Using polarizer adapted to separate polarized light beam oscillating perpendicularly to a plane including an axis of the incident light beam and an axis of the reflected light beam | | Using polarizer adapted to separate polarized light beam oscillating in parallel to a plane including an axis of the incident light beam and an axis of the reflected light beam | |
|---|---|---|---|---|---|---|
| | Orientation index value | Orientation angle (°) | Orientation index value | Orientation angle (°) | Orientation index value | Orientation angle (°) |
| 2 | 2.0000 | 0.0 | 2.0000 | 0.0 | 2.0000 | 0.0 |
| 3 | 0.0317 | −3.0 | 0.0317 | −3.8 | 0.0247 | −3.2 |
| 4 | 0.0597 | 0.0 | 0.0711 | 0.0 | 0.0467 | 0.0 |
| 5 | 0.0304 | −5.0 | 0.0357 | −4.9 | 0.0236 | −5.2 |
| 6 | 0.0327 | −4.2 | 0.0385 | −4.1 | 0.0260 | −3.9 |
| 8 | 0.0305 | −5.3 | 0.0362 | −5.0 | 0.0238 | −5.1 |
| 9 | 0.0302 | −5.3 | 0.0359 | −5.0 | 0.0237 | −5.2 |
| 10 | 0.0301 | −5.2 | 0.0360 | −4.9 | 0.0238 | −5.2 |
| 12 | 0.0301 | −5.2 | 0.0361 | −5.0 | 0.0236 | −5.2 |
| 15 | 0.0300 | −5.4 | 0.0359 | −5.0 | 0.0236 | −5.2 |
| 18 | 0.0300 | −5.4 | 0.0360 | −5.0 | 0.0237 | −5.2 |
| 20 | 0.0300 | −5.3 | 0.0360 | −5.0 | 0.0237 | −5.3 |

Intensity of the reflected light beam measured by a plurality of the light receiving means distributed substantially at equal angular distances on the circumference of a circle defined around the axis of the incident light beam Li in parallel to the paper surface is a periodic function (period of π) of the posture angle of each light receivers 20 and, as will be apparent from Table 1, the orientation index value as well as the orientation angles (periodic functions) calculated from the data acquired with eight or more light receivers 20, provide the necessary precision. Accordingly, it is preferred to use eight or more light receivers 20 and it is most preferable to use eight light receivers 20 in order to realize the light weight and small-sized apparatus of the invention as an on-line instrument.

Test 2

Figure 4A:
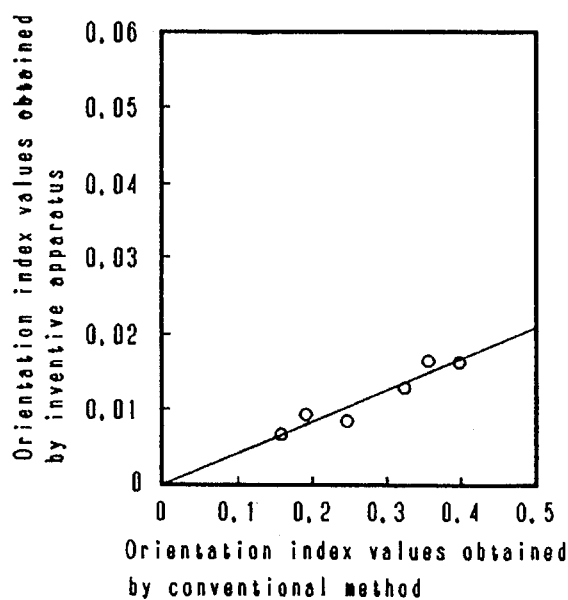
FIG. 4 is a diagram showing the fiber orientation characteristics of a given sample determined by the apparatus of the invention at an angle Θr of 30 degrees included between incident and reflected light beams without use of a polarizer as the light receiving means, on one hand, and actually determined by the conventional method, on the other hand, in which FIG. 4(a) indicates the orientation index values and FIG. 4(b) indicates the orientation angles.
Figure 4B:
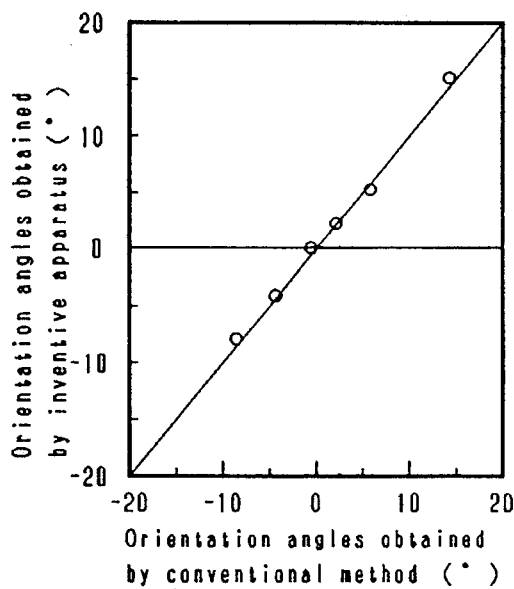
Figure 5A:
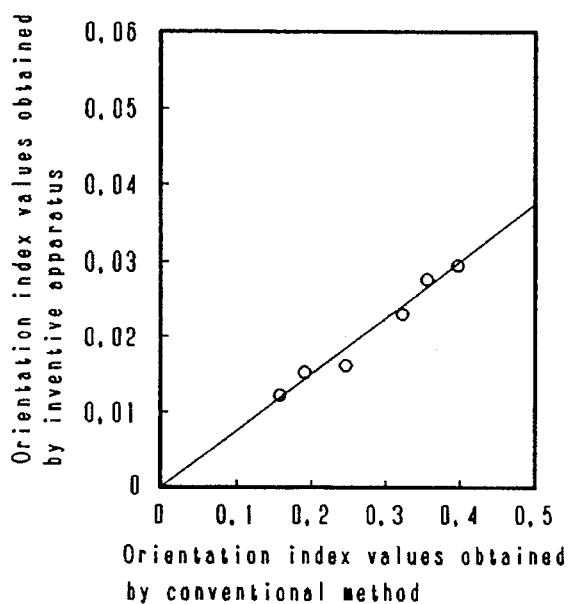
FIG. 5 is a diagram showing the fiber orientation characteristics of a given sample determined by the apparatus of the invention at an angle Θr of 50 degrees included between incident and reflected light beams without use of a polarizer as the light receiving means, on one hand, and actually determined by the conventional method, on the other hand, in which FIG. 5(a) indicates the orientation index values and FIG. 5(b) indicates the orientation angles.
Figure 5B:
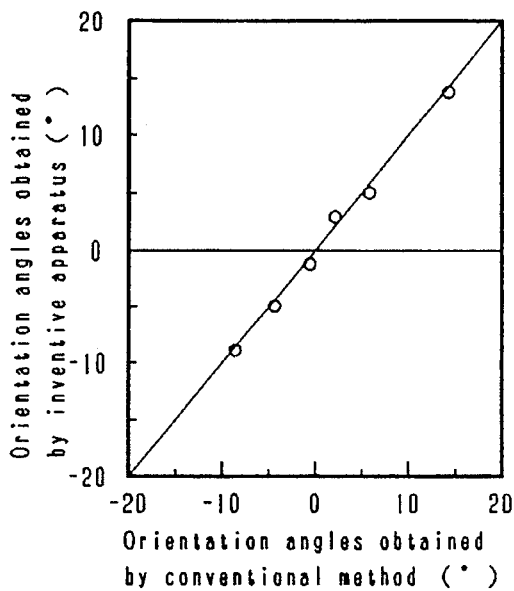
Figure 7A:
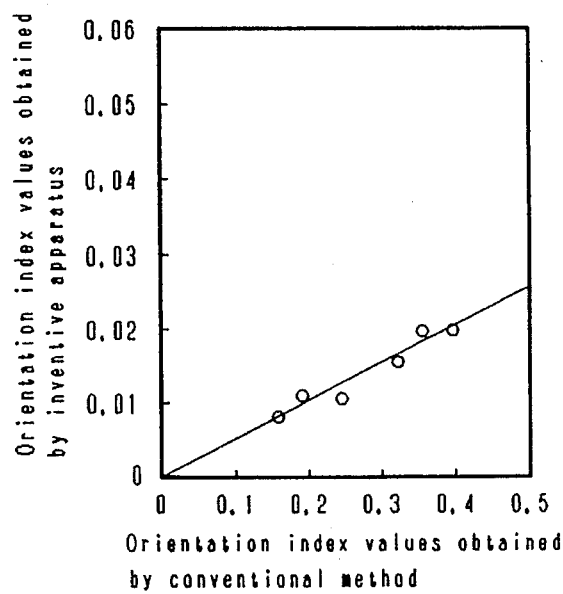
FIG. 7 is a diagram showing the fiber orientation characteristics of a given sample determined by the apparatus of the invention at an angle Θr of 30 degrees included between incident and reflected light beams using, as the light receiving means, a polarizer adapted to separate the polarized light beam oscillating perpendicularly to the plane including an axis of the incident light beam and an axis of the reflected light beam, on one hand, and actually determined by the conventional method, on the other hand, in which FIG. 7(a) indicates the orientation index values and FIG. 7(b) indicates the orientation angles.
Figure 7B:
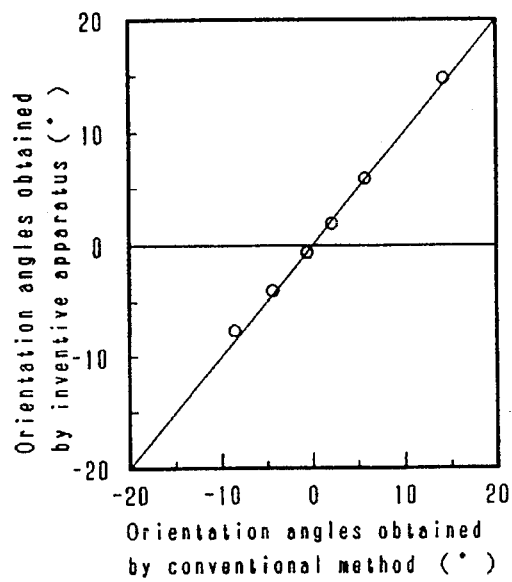
Figure 8A:
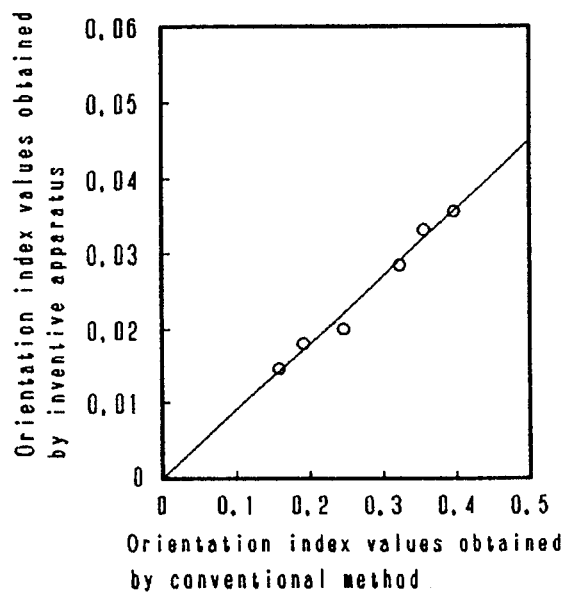
FIG. 8 is a diagram showing the fiber orientation characteristics of a given sample determined by the apparatus of the invention at an angle Θr of 50 degrees included between incident and reflected light beams using, as the light receiving means, a polarizer adapted to separate the polarized light beam oscillating perpendicularly to the plane including an axis of the incident light beam and an axis of the reflected light beam, on one hand, and actually determined by the conventional method, on the other hand, in which FIG. 8(a) indicates the orientation index values and FIG. 8(b) indicates the orientation angles.
Figure 8B:
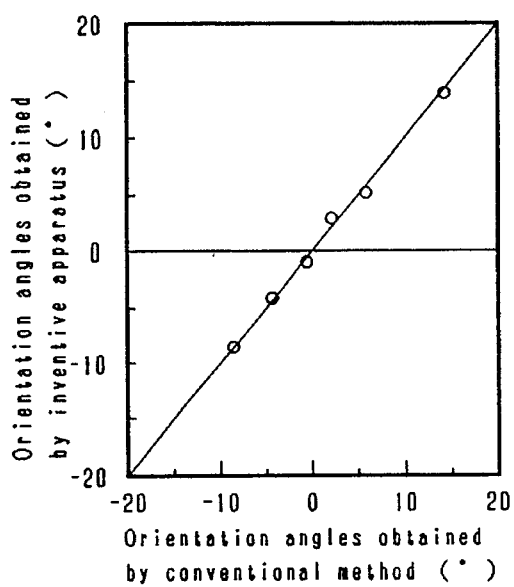
Figure 9A:
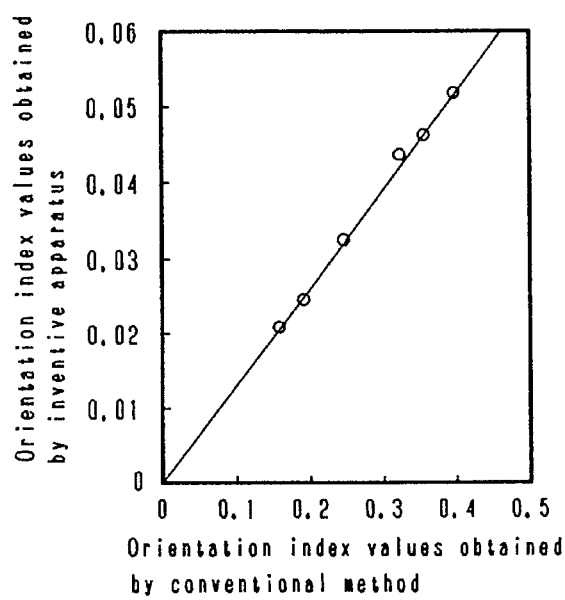
FIG. 9 is a diagram showing the fiber orientation characteristics of a given sample determined by the apparatus of the invention at an angle Θr of 70 degrees included between incident and reflected light beams using, as the light receiving means, a polarizer adapted to separate the polarized light beam oscillating perpendicularly to the plane including an axis of the incident light beam and an axis of the reflected light beam, on one hand, and actually determined by the conventional method, on the other hand, in which FIG. 9(a) indicates the orientation index values and FIG. 9(b) indicates the orientation angles.
Figure 9B:
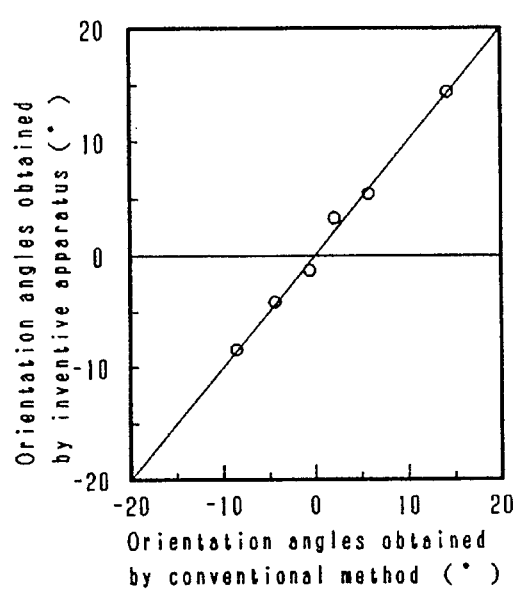
Figure 10A:
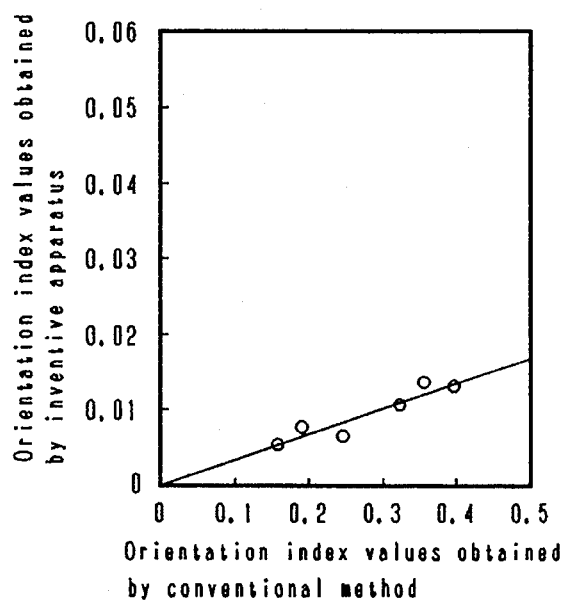
FIG. 10 is a diagram showing the fiber orientation characteristics of a given sample determined by the apparatus of the invention at an angle Θr of 30 degrees included between incident and reflected light beams using, as the light receiving means, a polarizer adapted to separate the polarized light beam oscillating in parallel to the plane including an axis of the incident light beam and an axis of the reflected light beam, on one hand, and actually determined by the conventional method, on the other hand, in which FIG. 10(a) indicates the orientation index values and FIG. 10(b) indicates the orientation angles.
Figure 10B:
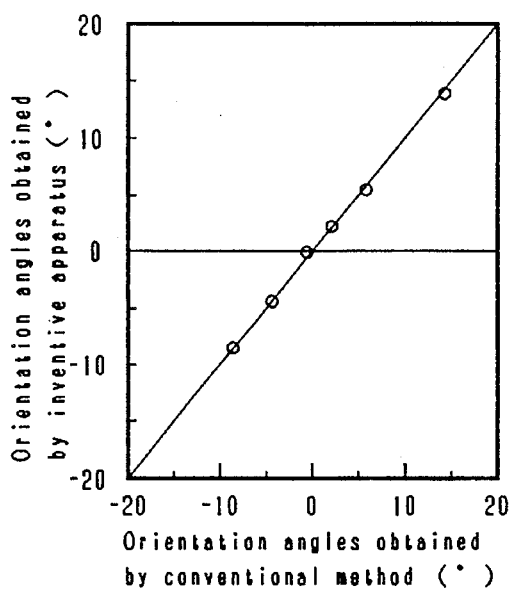
Figure 11A:
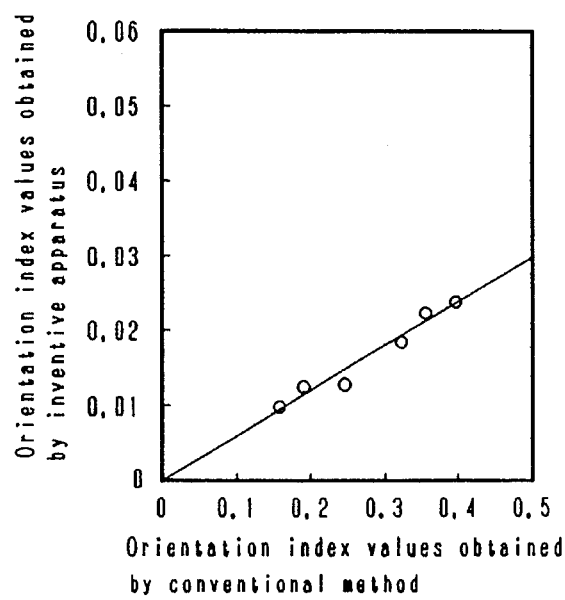
FIG. 11 is a diagram showing the fiber orientation characteristics of a given sample determined by the apparatus of the invention at an angle Θr of 50 degrees included between incident and reflected light beams using, as the light receiving means, a polarizer adapted to separate the polarized light beam oscillating in parallel to the plane including an axis of the incident light beam and an axis of the reflected light beam, on one hand, and actually determined by the conventional method on the other hand, in which FIG. 11(a) indicates the orientation index values and FIG. 11(b) indicates the orientation angles.
Figure 11B:
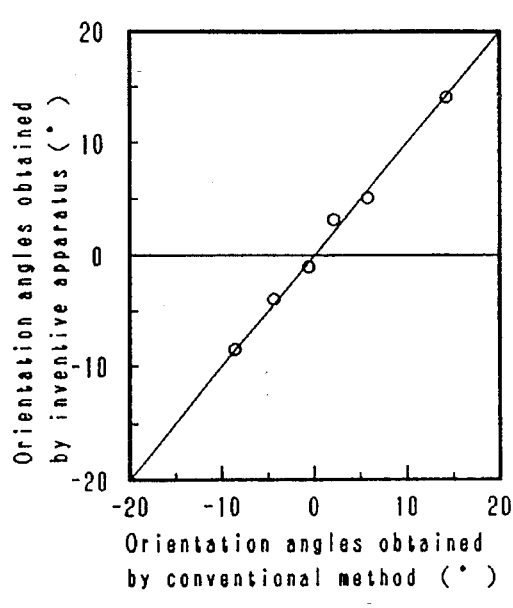
Figure 12A:
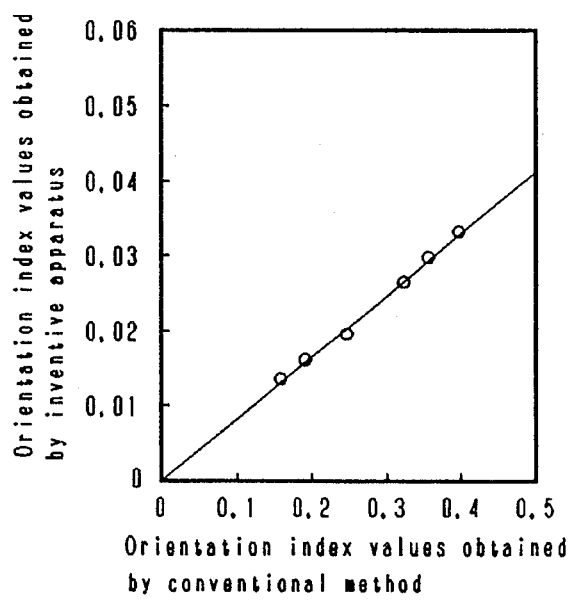
FIG. 12 is a diagram showing the fiber orientation characteristics of a given sample determined by the apparatus of the invention at an angle Θr of 70 degrees included between incident and reflected light beams using, as the light receiving means, a polarizer adapted to separate the polarized light beam oscillating in parallel to the plane including an axis of the incident light beam and an axis of the reflected light beam, on one hand, and actually determined by the conventional method, on the other hand, in which FIG. 12(a) indicates the orientation index values and FIG. 12(b) indicates the orientation angles.
Figure 12B:
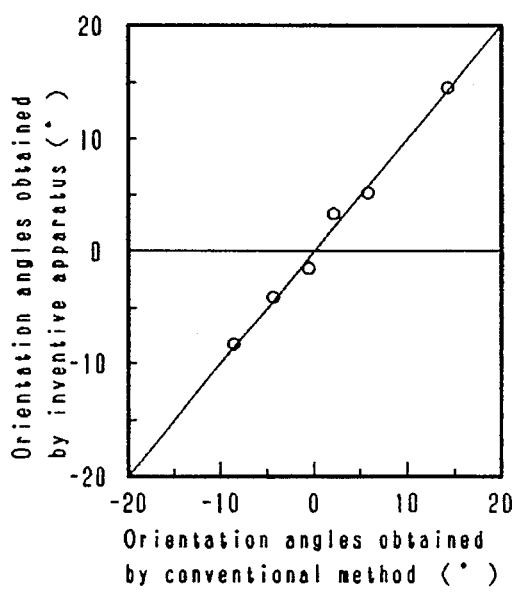

According to the conventional method, an experimental paper machine having directionality was used to make a sample (pulp slurry) mixed with dyed fibers and of the sheet FIGS. 4–6 show the data obtained using no polarizer 21 and at the angle Θr included between incident and reflected light beams adjusted to 30 degrees, 50 degrees and 70 degrees, respectively; FIGS. 7–9 show the data obtained using the polarizer 21 adapted to separate the polarized light beam oscillating perpendicularly to the plane including an axis of the incident light beam Li and an axis of the reflected light beam Lr and at the angle Θr adjusted to 30 degrees, 50 degrees and 70 degrees, respectively. FIGS. 10–12 show the data obtained using the polarizer 21 adapted to separate the polarized light beam oscillating in parallel to the plane including an axis of the incident light beam Li and an axis of the reflected light beam Lr and of the angle Θr adjusted to 30 degrees, 50 degrees and 70 degrees, respectively. In each of FIGS. 4–12, comparison of the orientation index values is shown by FIGS. 4(a)–12(a) and comparison of the orientation angles is shown by FIG. 4(b)–12(b).

Figure 6A:
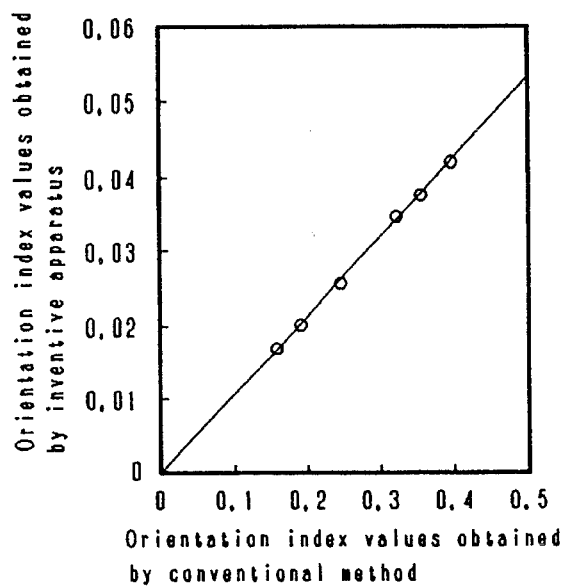
FIG. 6 is a diagram showing the fiber orientation characteristics of a given sample determined by the apparatus of the invention at an angle Θr of 70 degrees included between incident and reflected light beams without use of a polarizer as the light receiving means, on one hand, and actually determined by the conventional method, on the other hand, in which FIG. 6(a) indicates the orientation index values and FIG. 6(b) indicates the orientation angles.
Figure 6B:
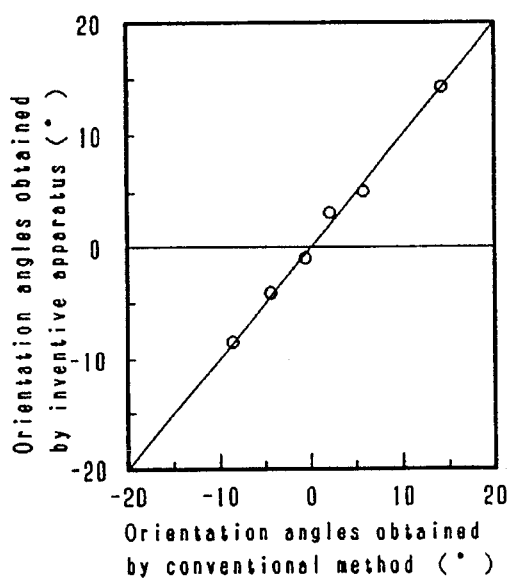

Referring to FIGS. 4–6 showing the result of determination using no polarizer 21, the orientation index values shown in FIGS. 4(a)–6(a) are highly correlated with the corresponding data obtained by the conventional method and the orientation angles shown in FIGS. 4(b)–6(b) take values similar to those obtained by the conventional method. It is found that the fiber orientation characteristics of the samples were determined with precision using the fiber orientation determining apparatus of the invention and a gradient of the straight line indicated in FIGS. 4(a)–6(a) becomes steeper as the angle Θr increases. It is thus found that the different fiber orientation characteristics depending on the paper samples were clearly revealed by the apparatus of the invention. As will be apparent from the data shown by these figures, both the result obtained using the polarizer 21 adapted to separate the polarized light beam oscillating perpendicularly to the plane including an axis of the incident light beam Li and an axis of the reflected light beam Lr shown by FIGS. 7–9, and the result obtained using the polarizer 21 adapted to separate the polarized light beam oscillating in parallel to the plane including an axis of the incident light beam Li and an axis of the reflected light beam Lr shown by FIGS. 10–12, are similar to the result obtained using no polarizer 21.

It should be understood that the determination according to the conventional method is a direct method by which an orientation of each fiber, as well as the number of the fibers presenting the same orientation are actually determined, and the determination using the apparatus of the invention is an indirect method by which the light intensity reflecting the fiber orientation is measured. In the respective figures, the orientation index values present different numbers of ciphers depending on the method of determination, but this is irrelevant to the accuracy so far as the differences in the fiber orientation characteristics depending on the paper sample should be determined. Concerning the orientation angles, the data obtained by the conventional method must be substantially coincident with the data obtained by the inventive apparatus.

At a fixed angle Θr between incident and reflected light beams, comparison of said three cases (i.e., the case using no polarizer 21, the case using the polarizer 21 adapted to separate the polarized light beam oscillating perpendicularly to the plane including an axis of the incident light beam Li and an axis of the reflected light beam Lr, and the case using the polarizer 21 adapted to separate the polarized light beam oscillating in parallel to the plane including an axis of the incident light beam Li and an axis of the reflected light beam Lr) indicates that independently of the angle Θr included between incident and reflected light beams, use of the polarizer 21 adapted to separate the polarized light beam oscillating perpendicularly to the plane including an axis of the incident light beam Li and an axis of the reflected light beam Lr makes the gradient of the straight line steeper and makes the difference of the fiber orientation characteristics depending on the paper samples more remarkable. In other words, the result of Test 2 indicates that the fiber orientation determining apparatus preferably comprises the light receiving means 20 each including the polarizer 21 adapted to separate the polarized light beam oscillating perpendicularly to the plane including an axis of the incident light beam Li and an axis of the reflected light beam Lr and is operated at the angle Θr included between incident and reflected light beams adjusted to an angle as wide as possible.

Test 3

Figure 13:
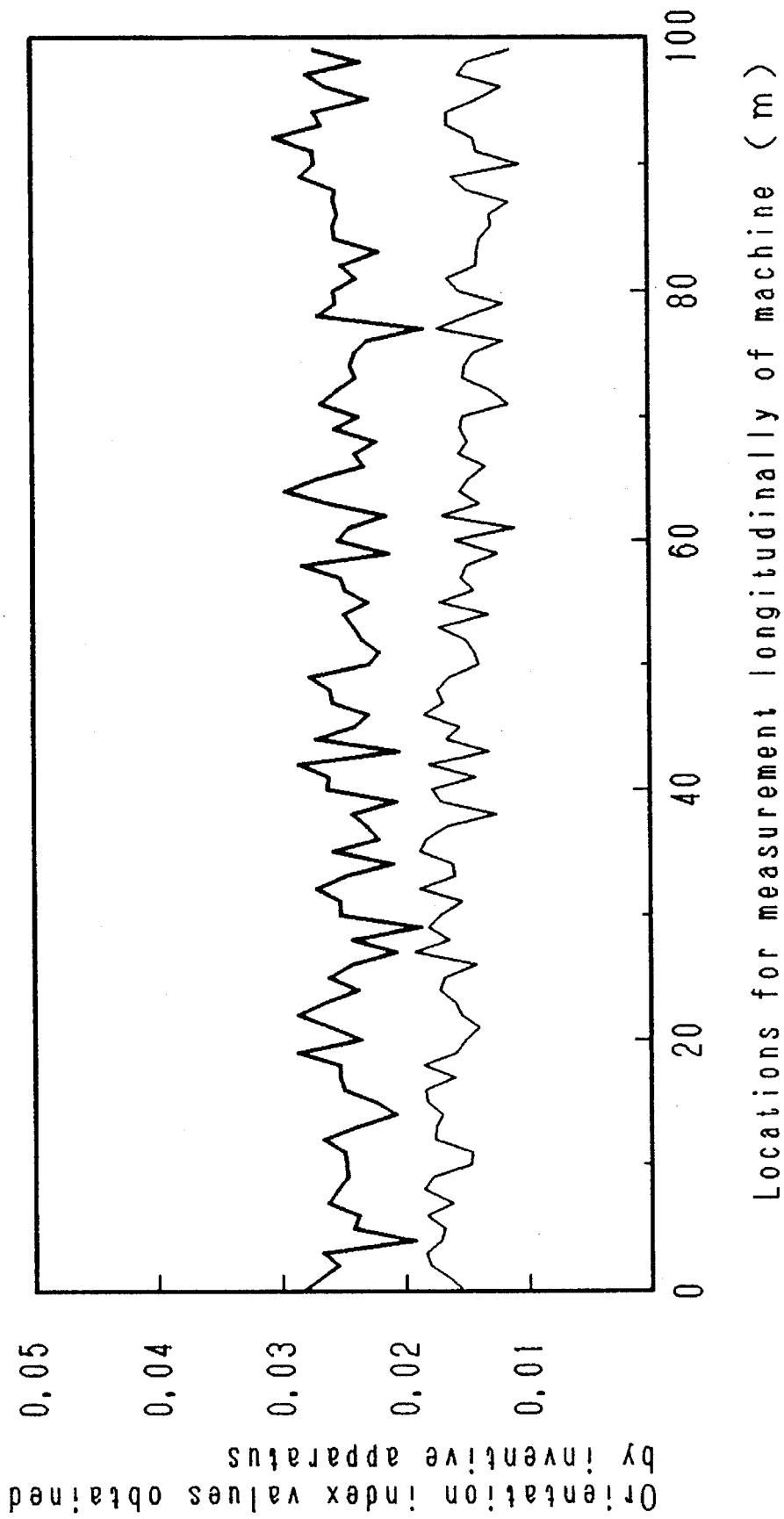
FIG. 13 is a diagram showing the orientation index values determined by the apparatus of the invention installed on a paper machine of long wire type, said apparatus using, as the light receiving means, a polarizer adapted to separate the polarized light beam oscillating perpendicularly to the plane including an axis of the incident light beam and an axis of the reflected light beam and said determination being performed at an angle Θr of 50 degrees included between incident and reflected light beams, in which the result of measurement on the surface of the paper web facing the wire is indicated by a thick solid line and the result of measurement on the surface of the paper web facing the felt is indicated by a thin solid line.
Figure 14:
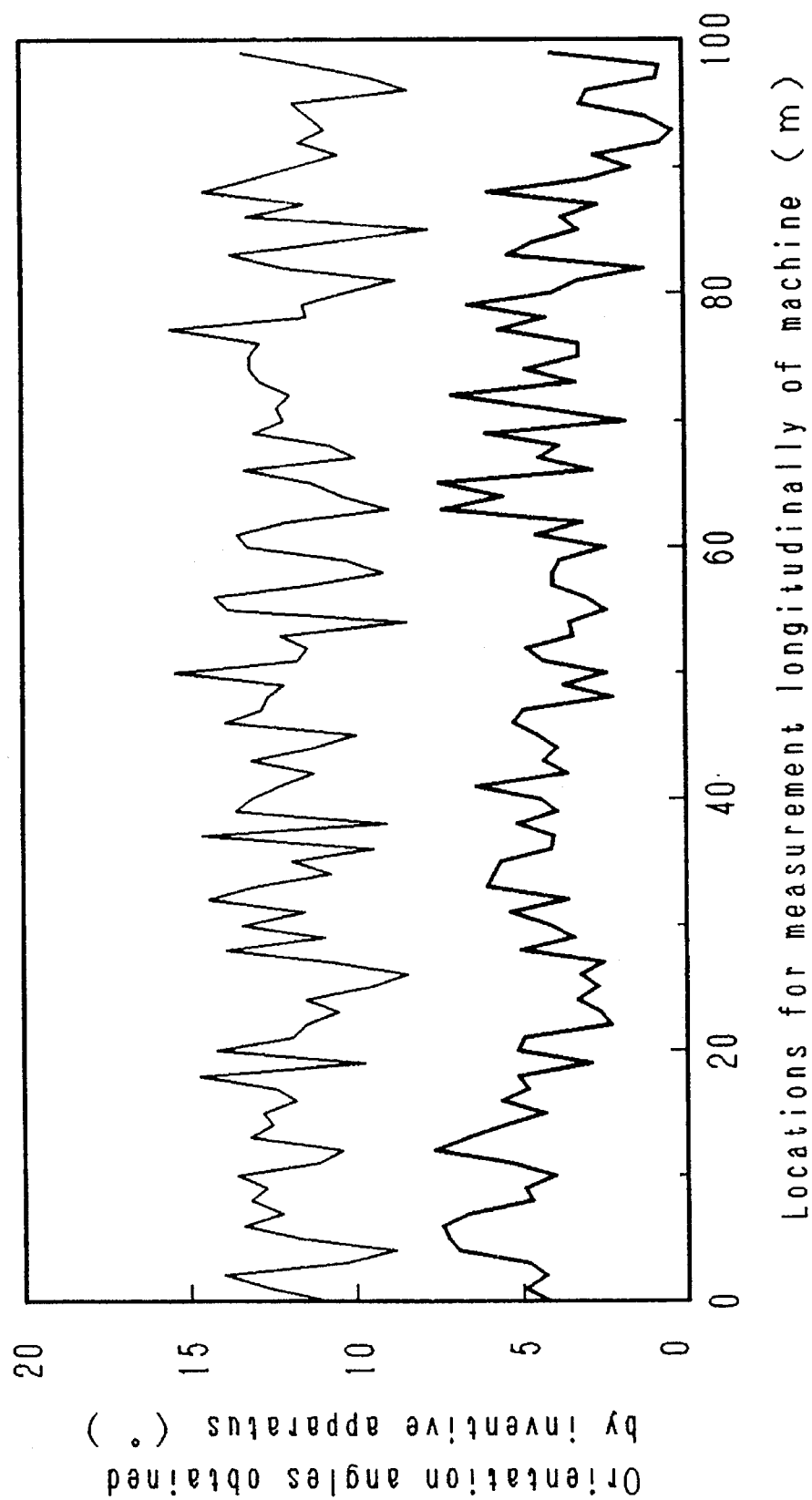
FIG. 14 is a diagram showing the orientation angles determined by the apparatus of the invention installed on the paper machine of long wire type, said apparatus using, as the light receiving means, a polarizer adapted to separate the polarized light beam oscillating perpendicularly to the plane including an axis of the incident light beam and an axis of the reflected light beam and said determination being performed at an angle Θr of 50 degrees included between incident and reflected light beams, in which the result of measurement on the surface of the paper web facing the wire is indicated by a thick solid line and the result of measurement on the surface of the paper web facing the felt is indicated by a thin solid line.

The fiber orientation characteristics of the PPC paper having a weight per unit area of 64 g/m² moving in a paper machine of long wire type at a speed of 620 m/min were determined on both sides of this web, (i.e., on the side thereof facing the wire and on the side thereof facing the felt) using the fiber orientation determining apparatus similar to that which had been used in Test 1. The apparatus was provided with eight light receivers 20 each including the polarizer 21 adapted to separate the polarized light beam oscillating perpendicularly to the plane including an axis of the incident light beam Li and an axis of the reflected light beam Lr, at the angle Θr of 50 degrees included between incident and reflected light beams. The orientation index values and the orientation angles obtained from this test are shown in FIGS. 13 and 14, respectively. Referring to FIGS. 13 and 14, the data obtained on the side of the paper web facing the wire are indicated by a thick solid line and the data obtained on the side of the paper web facing the felt are indicated by a thin solid line.

It is indicated by the data that said paper web presents the orientation index values larger on its wire side than on its felt side and the orientation angles larger on its felt side than on its wire side.

As will be apparent from the foregoing description, the method and the apparatus of the invention for determining the paper fiber orientation not only allow any rotatable member to be eliminated from the optical system, but also allow the determination to be rapidly performed. This result is achieved by the invention, wherein the unpolarized light beam is directed to the paper surface and the light beam reflected by the paper surface is simultaneously caught by a plurality of light receivers to determine the fiber orientation characteristics. In addition, the apparatus of the invention can be easily miniaturized since it requires no rotatable member. Furthermore, the apparatus of the invention can achieve the desired determination without coming in contact with, and destroying, the paper web.

Allowing the time taken for determination to be substantially shortened, the apparatus of the invention can easily and precisely determine the fiber orientation characteristics of the paper web moving at a high speed in the paper machine, such that the apparatus may be installed on the paper machine to achieve the on-line determination. Moreover, a pair of the apparatuses may be installed on the paper machine on both sides of the paper web in a mutually opposing relationship to achieve determination, as well as comparison, of the fiber orientation characteristics obtained both surfaces of the paper web, i.e., on the surface thereof facing the wire and on the surface thereof facing the felt. Accordingly, the result of determination can be rapidly fed back to the actual operating condition of the paper machine and thereby the quality of the paper being made can be improved.

Additionally, distribution of the fiber orientation in a desired direction can be determined for each sample sheet and, when the determination is carried out simultaneously on both sides of a given sample sheet facing the felt and wire, respectively, a differential distribution of the fiber orientation between these two sides of this sample sheet can be determined. These features of the invention may be effectively utilized to monitor and control the quality of the sample sheet.

Although the invention has been described with respect to specific preferred embodiments thereof, many variations and modifications will become apparent to those skilled in the art. It is, therefore, the intention that the appended claims be interpreted as broadly as possible in view of the prior art to include all such variations and modification.

The embodiments of the invention in which an exclusive property or privilege is claimed are defined as follows.

1. A method for determining the fiber orientation of paper comprising the steps of:

projecting an unpolarized light beam perpendicularly to a surface of paper which is at a standstill or moving;

measuring the intensity of a light beam reflected by the surface of the paper substantially in the same instant at eight or more locations distributed on the circumference of a circle on the side of the paper upon which the unpolarized light beam is incident, the circle defined in a plane extending in parallel to the surface of the paper and around a point at which an axis of the incident light beam intersects the plane; and calculating fiber orientation characteristics of the paper, such as the fiber orientation index value and the fiber orientation angle, from the intensity of the reflected light beam measured at the eight or more locations of the circle.

2. The method for determining the fiber orientation of paper according to claim 1, wherein unpolarized light beams are projected perpendicularly to opposite surfaces of the paper and the light beams reflected by the paper are detected on the respective sides of the paper.

3. The method for determining the fiber orientation of paper according to claim 1, wherein said measuring includes polarizing the reflected light beam to oscillate perpendicularly to a plane including an axis of the incident light beam and an axis of the reflected light beam and measuring the intensity of the polarized light beam.

4. The method for determining the fiber orientation of paper according to claim 1, wherein said measuring includes polarizing the reflected light beam to oscillate in parallel to the plane including an axis of the incident light beam and an axis of the reflected light beam, both being separated from the beam reflected by the paper surface, and measuring the intensity of the polarized light beam.

5. The method for determining the fiber orientation of paper according to claim 1, wherein the intensity of the light beam reflected by the paper surface is measured at locations distributed at substantially equal angular intervals on the circumference of a circle on the incident side of the unpolarized light beam, the circle defined in a plane extending in parallel to the paper surface around the point at which the axis of the incident light beam intersects said plane.

6. A method for determining the fiber orientation of paper while on-line, comprising the steps of:

projecting an unpolarized light beam perpendicularly to a surface of the paper moving in a paper machine;

measuring the intensity of a light beam reflected by the surface of the paper substantially in the same instant at eight or more locations distributed on a circumference of circle, on the side of the paper upon which the unpolarized light beam is incident, the circle defined in a plane extending in parallel to said surface of the paper and around a point at which an axis of the unpolarized light beam intersects the plane;

scanning a spot on the surface of the paper being illuminated by the unpolarized light beam transversely of the paper machine; and calculating fiber orientation characteristics of the paper, including the fiber orientation index value and the fiber orientation angle, from the intensity of reflected light beam measured at each of the eight locations.

7. The method for determining the fiber orientation of paper according to claim 6, wherein unpolarized light beams are projected perpendicularly to opposite surfaces of the paper and the light beams reflected by the paper are detected on the respective sides of the paper.

8. The method for determining the fiber orientation of paper according to claim 6, wherein said measuring includes polarizing the reflected light beam to oscillate perpendicularly to a plane including an axis of the incident light beam and an axis of the reflected light beam and measuring the intensity of the polarized light beam.

9. The method for determining the fiber orientation of paper according to claim 6, wherein said measuring includes polarizing the reflected light beam to oscillate in parallel to the plane including an axis of the incident light beam and an axis of the reflected light beam, both being separated from the beam reflected by the paper surface, and measuring the intensity of the polarized light beam.

10. The method for determining the fiber orientation of paper according to claim 6, wherein the intensity of the light beam reflected by the paper surface is measured at locations distributed at substantially equal angular intervals on the circumference of a circle on the incident side of the unpolarized light beam, the circle defined in a plane extending in parallel to the paper surface around the point at which the axis of the incident light beam intersects said plane.

11. An apparatus for determining the fiber orientation of paper, said apparatus comprising:

a projector for projecting an unpolarized light beam perpendicularly to a surface of paper which is at a standstill or moving;

eight or more light receivers distributed on the circumference of a circle defined by a plane extending in parallel to the surface of the paper and having a center of a point where an axis of the incident light beam intersects the plane, each light receiver including photoconductive elements adapted to measure the intensity of a light beam reflected by the surface of the paper;

a light information processor coupled to said receivers and adapted to process a signal representing an intensity of the reflected light beam measured by each of said light receivers and applied to said light information processor to output a light intensity information signal; and an arithmetic circuit to calculate fiber orientation characteristics such as a fiber orientation index value and a fiber orientation angle from the output signal of said light information processor.

12. An apparatus for determining the fiber orientation of paper in a paper machine, said apparatus comprising:

a projector to project an unpolarized light beam perpendicularly to an incident surface of paper moving in the paper machine;

eight or more light receivers distributed on the incident surface side of the paper and around a circumference of a circle defined in a plane extending in parallel to the incident surface of the paper and having a center point at which an axis of the incident light beam intersects the plane, each of the light receivers including photoconductive elements adapted to measure the intensity of a light beam reflected by the incident surface of the paper;

a light information processor coupled to said light receivers for processing a signal representing an intensity of the reflected light beam measured by each of the light receivers and applied to the processor to output a light intensity information signal;

an arithmetic circuit to calculate fiber orientation characteristics such as a fiber orientation index value and a fiber orientation angle from the output signal of the light information processor; and said projector means and said light receivers scanning the paper transversely of the paper machine.

13. The apparatus for determining the fiber orientation of paper according to claim 12, wherein said paper has a felt side surface and a wire side surface and wherein a projector is positioned on both sides of the paper to illuminate the felt and wire side surfaces of the paper and light receivers positioned on the felt and wire side surfaces to catch the light beams reflected by the felt and wire surfaces of the paper.

14. The apparatus for determining the fiber orientation of paper according to claim 13, wherein each of said light receivers includes a polarizer adapted to separate from the reflected light beam a polarized light beam oscillating perpendicularly to or in parallel to a plane including an axis of the incident light beam and an axis of the reflected light beam.

15. The apparatus for determining the fiber orientation of paper according to claim 14, wherein said eight or more light receivers are distributed at substantially equal angular intervals on the circumference of the circle.

* * * * *